United States Patent
Yvin et al.

(10) Patent No.: US 6,660,722 B2
(45) Date of Patent: Dec. 9, 2003

(54) THERAPEUTICAL TREATMENTS

(75) Inventors: Jean-Claude Yvin, Saint-Malo (FR); Vaclav Vetvicka, Louisville, KY (US)

(73) Assignee: Laboratoires Goemar S.A., Saint-Malo (FR)

( * ) Notice: Subject to any disclaimer, the term of this patent is extended or adjusted under 35 U.S.C. 154(b) by 0 days.

(21) Appl. No.: 09/999,202

(22) Filed: Nov. 30, 2001

(65) Prior Publication Data

US 2003/0119780 A1 Jun. 26, 2003

(51) Int. Cl.$^7$ .............................. C08B 37/18; C07H 1/08
(52) U.S. Cl. ................. 514/54; 536/123.12; 536/123.1; 536/124; 536/122
(58) Field of Search ....................... 514/54; 536/123.12, 536/124, 123.1, 122

(56) References Cited

PUBLICATIONS

Marcuccio et al. Accad.Pugliese Sci., Atti Relaz., Parte 2 (1967), 25 (Pt. 2), 327–35.*
Arinaga, Shinya et al., "Enhanced production of Interleukin 1 and tumor necrosis factor by peripheral monocytes after lentinan administration in patients with gastric carcinoma", Int. J. Immunopharmacol., 1992, pp. 43–47, vol. 14, No. 1.
Chihara, G., "Immunopharmacology of Lentinan and Glucans", Immunol. Immunopharmacol., 1983, pp. 85–96, vol. 5.
Chihara, G. et al., "Antitumor and Metastasis–Inhibitory Activities of Lentinan as an Immunomodulator", Cancer Detection and Prevention Supplement, 1987, pp. 423–443, vol. 1.
Dennert, Gunther and Derek Tucker, "Antitumor Polysaccharide Lentinan—A T Cell Adjuvant", Journal of the National Cancer Institute, Nov. 1973, pp. 1727–1729, vol. 51, No. 5.
Fachet, Jozsef et al., "Effect of lentinan on different types of immune responses including anaphylactic shock". (Publication information to follow).
Tazawa, K. et al., "Inhibitory effect of lentinan entrapped in liposomes on pulmonary metastasis in rats. Distribution of liposomes and enhancement of NK cell activity", J. Exp. Clin. Cancer Res., 1992, pp. 21–27, vol. 11, No. 1.
Vervicka, Vaclav, "β–Glucans as Immunomodulators", JANA, Winter 2001, pp. 13–16, vol. 3, No. 4.

* cited by examiner

Primary Examiner—Samuel Barts
Assistant Examiner—Michael C. Henry
(74) Attorney, Agent, or Firm—Kilpatrick Stockton LLP

(57) ABSTRACT

Therapeutical method comprising administration to a patient of an effective amount of especially soluble laminarin for the treatment of tumors and more generally of cancers of the group comprising breast cancer, lung cancer, oesophagus cancer, stomach cancer, intestine and colon cancers, and for the treatment of viral, bacterial and fungal diseases as well as diseases related to immunostimulant deficiencies of human beings and warm-blood animals.

11 Claims, No Drawings

THERAPEUTICAL TREATMENTS

The invention relates to therapeutical treatments.

More particularly it relates to therapeutical treatments based on the immunostimulant antitumoral and cytokine synthesis-inducing and -accelerating activities of laminarin, especially of soluble laminarin, a well known glucan, which activities were surprisingly and unexpectedly discovered by the Applicants in the course of extensive and thorough studies and searches and on which are founded the hereafter disclosed and claimed applications and uses.

The therapeutical treatments in question are intended to treat cancers, viral, bacterial and fungal diseases as well as diseases related to immunostimulant deficiencies of human beings and warm-blood animals.

The Applicant's discovery is all the more important and unexpected as comparative test, which are hereafter disclosed, show the superiority from the point of view of efficiency of especially the soluble form of laminarin with respect to another glucan, i.e. lentinan, which is extracted from a mushroom and which is used in Japan since 25 years as an adjunctive in antitumor therapy, and as glucans of the laminarin and pachyman type (single helical form) were considered as "antitumor negative" i.e. as not having antitumor properties in comparison with glucans of the family comprising lentinan, curdlan, schizophyllan and pachymaran (triple helical form) which were considered as "antitumor positive" i.e. as acting against tumors. (see G. CHIHARA, National Cancer Center Research Institute, Tokyo, Japan, article under the title "Immunopharmacology of lentinan and glucans", published in EOS-Riv.Immunol.Immunopharmacol., 5:85, 1983).

Another important aspect of the invention comes from the fact that it makes available therapeutical treatments which permit to fight again the increasing occurrence of antibiotic-resistant, nosocomial infections which are often untreatable by classical procedure, the treatments of these diseases by immunomodulators such as cytokines, while efficient, being associated with the inherent toxicity of these materials.

Laminarin is extracted from brown algae and its molecular weight is from about 2500 to about 6000.

Laminarin is consisting of a main linear chain of 15 to 35 glucopyranose units joined by acetalic $\beta$-(1,3) linkages and to which a low proportion of branches, in essentially primary position of principally $\beta$-D-glucopyranose units are joined by $\beta$-(1,6) linkages, some of these $\beta$-D-glucopyranose units being joined to the main chain.

The average degree of polymerisation is close to 25.

The terminal unit of the main chain is consisting of glucose or of mannitol, thus providing two types of molecules respectively called G or M.

Complete hydrolysis provides glucose and manitol.

Two forms of laminarin have been identified; one of these forms is the here preferably used soluble form, while the other one is insoluble in water, the latter being probably characterized by few or even no branches.

Both the soluble and the insoluble form may be obtained by extraction from e.g. laminaria species; two of these species are laminaria digitata and laminaria hyperborea.

Soluble laminarin occurs under the form of a white to beige powder which is odourless and tasteless; the soluble form is very hygroscopical and water-soluble (up to 60 g/l), while being substantially insoluble in ethanol, 2-propanol and acetone.

The identification of soluble laminarin may be carried out by way of liquid chromatography using, for example, a device comprising an amperometric detector.

Procedure may be as follows, using an anion-exchange column, fitted with a non-porous, polymeric resin whose particle size is about 5 $\mu$m, the length of the column being 250 mm and the internal diameter 4 mm, a pulsed amperometric detector equipped with a gold electrode, a mobile phase consisting of the mixture of a solution A with a solution B, the solution A initially representing 30% and the solution B 70%, the latter becoming isocratic of A after 4 minutes, which means that the mobile phase is only consisting of A.

Solution A is obtained by dissolving 41 g of sodium acetate in 950 ml of water, free of particles, and by introducing 8.2 ml of NaOH of 46–48%.

Solution B is 150 mM solution of NaOH obtained by mixing 8.2 ml of NaOH of 47% with 990 ml of water, free of particles.

A quantity of 50 ml of the solution to be examined is injected and eluted at a rate of 1 ml/min during 15 minutes.

The thus obtained chromatogramm comprises a Gauss pic of retention comprised between 5.8 and 12 minutes, of maximum amplitude located at about 8 minutes.

The pH of a solution of 1 g of soluble laminarin in water, free of carbon dioxyde, completed to 10 ml, is from 6.5 to 7.5.

The combustion residue of 1 g of soluble laminarin is not higher than 5%.

The fucan content of soluble laminarin obtained by liquid chromatography dosing of the fucose content of the product obtained by total hydrolysis of the said soluble laminarin appears to be lower than 5%.

As mentioned hereabove, laminarin is extracted from brown macrophytic marine algae of the Pheophyceae type, in particular from fucales or laminariales.

Various extraction methods can be used.

Reference may be made for example to the method described by Black et al., Appl. Chem. 1951, 1, pages 505 to 517.

More generally, laminarin can be obtained from brown algae by any extraction process provided it enables the constituents other than laminarin (wall polysaccharides, salts, etc.) to be successively removed.

In particular, these processes use steps involving grinding, precipitation in an acid or basic medium, ultrafiltration and dialysis.

The thus obtained product is consisting of a mixture of the soluble and the insoluble forms of laminarin, the respective proportions of which vary according to the selected algae.

For example, laminaria digitata or laminaria saccharina provide a mixture comprising about 90% by weight of the soluble form, while laminaria hyperborea provides a mixture comprising about 80% by weight of the insoluble form.

The latter is separated by precipitation.

The following non-limiting example illustrates the extraction process of soluble laminarin.

EXAMPLE 1

Process for the Extraction of Soluble Laminarin from Laminaria Saccharina 300 g of fresh algae of the Laminaria saccharina type, harvested in August, are subjected to cryobursting (–40° C.) by the process described in French patent no. 74 35162.

The product thus obtained has a mean particle diameter of between 50 and 100 $\mu$m and a solids content of 10–12%. A quantity of 0.9 l of 0.3% sulfuric acid is added gradually to 300 g of this product. Extraction is performed in a water bath at a temperature of about 80° C., for 1 hour, will stirring.

This operation is repeated twice.

After neutralization, the extract obtained is treated with polyvinylpyrrolidone in a dose of about 1% by weight. This is done by introducing 9 g of polyvinylpyrrolidone (PVP) into a volume of 90 ml of extract. The PVP is left to thicken for about 2 hours. The resulting solution is added to abut 0.9 liter of extract, the mixture being stirred for 30 min and then filtered under vacuum on a Whatman GF/A filter.

The thus obtained liquid is subjected to tangential ultra-filtration on a carbon-ceramic tubular membrane of the "Carbosep" type with a porosity of 50,000 Daltons. A pressure of 1 bar is maintained on the filtration column during the operation.

This gives a filtrate having a volume of about 0.8 liter and a pH of 5.5. The filtrate is maintained about one night at about 4° C.; the precipitated insoluble form of laminarin is removed by filtration and the thus treated filtrate is then dialyzed on a cellulose ester membrane of the SPECIRA Pore type with a porosity of 500 or 1000 Daltons. The dialyzate is then lyophilized to give 7 g of dry powder, corresponding to pure soluble laminarin.

In the course of the above mentioned studies and searches carried out especially on soluble laminarin, the Applicants performed more particularly experimentations to determine its ability to act on the defence reactions responsible for cytotoxicity.

In that respect, Applicants first carried out an in vitro cytotoxicity assay on spleen cells isolated from spleen of Balb/c mice by standard methods.

These tests were conducted to evaluate the effects of soluble laminarin on the cytotoxicity of NK (Natural Killer) cells of mouse and to compare these effects with those of two known glucans, ie.
1. a yeast-derived glucan called BEI and purchased from the firm Biopolymer Engineering, In., St. Paul, Minn., USA and
2. the above-mentioned lentinan which is purchased from the firm Sigma St. Louis, Mo., USA), lentinan being a 1,3-β-D-glucan which can be isolated from the edible mushroom called *Lentinius edodes*.

The spleens isolated from the above said Balb/c mice were placed into Petri dishes containing RPMI 1640 medium obtained from Life Technologies USA, supplemented with 5% by weight of FCS (fetal calf serum from Life Technologies USA). The spleens were cut into small pieces and a suspension was made by pressing the minced spleens against the bottom of Petri dishes containing PBS (Phosphate Buffered Saline obtained from Biowhitaker Inc, 8830 Biggsford Road, Walkersville, Md. 21793 USA). The thus obtained pieces of tissue were gently teased over stainless steel screens using a plunger of a 5-ml syringe. Large debris and cell clumps were removed by layering the cell suspension over 3 ml of heat-inactivated FCS for 10 minutes on ice. After elimination of erythrocytes by incubation during 10 seconds in distilled water and five washes in cold PBS, the thus obtained cells which are called splenocytes, were resuspended in PBS and counted.

Procedure was as follows

An amount of 0.25 ml of trypan blue (obtained from Sigma) solution (0.4% w/v in water) was mixed with 0.15 ml PBS and 0.1 ml of the above cell suspension (which comprises $2.6\times10^6$ cells/ml).

The resulting mixed solution was allowed to stand for 5 min at room temperature.

Then a small amount of the suspension was transferred either to an hemocytometer chamber or an a cover glass and the cells counted under a microscope.

Non viable cells could be easily identified as they were stained in blue.

The viability of the cells, represented by V %, is determined using the formula:

$$V\% = \frac{\text{Number of viable cells}}{\text{Number of viable cells} \times \text{number of non viable cells}} \times 100$$

Only cell suspensions for which V % was found to be higher than 95% were used in the subsequent experiments.

The evaluation of the cytotoxicity of these cell suspensions was conducted by suing a non radioactive cytotoxicity assay marketed under the trademark CYTOTOX 96 by Promega, Madison, Wis., USA.

For these experiments, the splenocytes which are also called "effector cells" were pre-treated during 30 minutes by mixing the suspensions containing them respectively with soluble laminarin, with lentinan and with BEI glucan; the mixtures were subsequently incubated with suspensions of target cells of tumor cell line YAC-1 which is known to be relatively resistant to normal inactivated N K cells.

The specificity of the assay was established by using the following three different ratios effector cells/target cells denoted ET: 10:1, 50:1 and 100:1.

For each ratio, 3 counts were carried out and experiments were repeated 3 times on 3 different days.

Controls consisted of effector cells incubated only with PBS.

More particularly, the above cell suspensions of splenocytes (effector cells) were diluted to $10^6$ cells/ml and placed in individual wells of V-shaped 96-well microplates at a concentration of 0.1 ml/well.

Laminarin, lentinan and BEI glucan which occur in the form of powders, were added after dissolution in PBS at an identical concentration of 2 µg/ml in PBS and the plates were incubated for 30 minutes at 37° C. in an humidified $CO_2$ incubator.

After incubation, the plates i.e. the incubated cells contained in the wells were washed three times with RPMI 1640 medium, and 50 µl of the suspension of target cell line YAC-1 were added in each well, respecting the above "effector cells/target cells" ratios or E T: 10:1, 50:1 and 100:1.

For each of these ratios, 3 individual wells were used, the number of target cells being respectively $10^4, 2\times10^3$ and $1\times10^3$.

In addition, target cells for spontaneous release control, target cells for maximum release control and effector cells release control were introduced into appropriate wells, i.e. 3 individual wells for each concentration used.

The expressions spontaneous release control, maximum release control and effector cells release control respectively mean Target cells spontaneous LDH release LDH release from wells with target cells only after addition of lysis solution Effector cells (NK cells) spontaneous LDH release.

Basically, it is necessary to obtain the values of spontaneous release from both target and effector cells, and these values serve as a background. The maximum release control serves as 100%.

After spinning the plates at 250 g for 5 minutes in a centrifuge, the plates were incubated for 4 hours at 35° C. in a humidified $CO_2$ incubator.

For evaluating the cytotoxicity activity of the effector or NK cells, procedure was as follows, using the instructions of the manufacturer PROMEGA.

Here again, use was made of the non radioactive Cytotoxicy Assay KIT marketed under the trademark CYTOTOX 96 by PROMEGA.

A quantity of 10 μl of lysis solution, included in the Kit, was added 45 min before the end of incubation into appropriate control wells, i.e. into wells with maximum release control.

Next step was spinning the plates at 250×g for 5 min in the centrifuge, followed by transfer of 50 μl of supernatant into the wells of flat-bottom 96-well microplates.

A quantity of 50 μl of reconstituted substrate (12 ml of assay buffer added to a bottle of substrate mix and used as reconstituted substrate) was added into each well; then the plates were covered and incubated for 30 minutes at room temperature at dark.

The optical density of each well was then determined at 492 mm using a reader consisting of a kit marketed by Tecan U.S., Research Triangle Park, N.C. under the trademark STL ELISA.

The specific cell-mediated cytotoxicity was calculated using the following formula disclosed in the manufacturer's instruction comprised in the kit:

$$\% \text{ cytotoxicity} = \frac{100(OD_{492} \text{ experimental} - OD_{492} \text{ spontaneous})}{OD_{492} \text{ maximum} - OD_{492} \text{ spontaneous}}$$

wherein

"$OD_{492}$ experimental" is the optical density measured at 492 nm of target cells lysed in presence of effector cells "$OD_{492}$ spontaneous" is the spontaneous release i.e. the optical density measured at 492 nm of the suspension of target cells incubated with medium alone and "$OD_{492}$ maximum" is the maximum release i.e. the optical density measured at 492 nm of target cells lysed with the solution provided in the kit.

For each of laminarin, BEI, Lentinan and the control, three experiments were carried out at each of the above identified three "effector cells/target cells" ratios.

From the average value of the three experiments in each case the average percentage of killed cells was determined.

The thus determined percentages are collected in the following Table I.

TABLE I

| Effector cells/target cells ratio (ET) | % of Killed cells (recorded value and standard deviation) | | |
| --- | --- | --- | --- |
| | ET = 10:1 | ET = 50:1 | ET = 100:1 |
| Lentinan | 40.1 + 4.6 | 46.3 + 2.3 | 52.8 + 2.4 |
| BEI | 36.2 + 4.9 | 46.8 + 2.4 | 56.3 + 2.6 |
| Laminarin | 48.1 + 4.4 | 57.3 + 5.3 | 72.7 + 5.5 |
| Control | 19.6 + 7.1 | 29.2 + 3.9 | 40.4 + 4.8 |

On the graphical representation of the herewith attached FIG. 1, the percentage of killed cells collected in table I is plotted on the Y axis; on the X axis are represented the above said three ratios in connection with each product tested, i.e. soluble laminarin, BEI, Lentinan and the control.

The hereafter commented conclusions can be drawn from examination of FIG. 1.

As a function of the increase of the value of ET, the controls (effector cells incubated with PBS only) showed a steady increase in killing of target cells.

The comparison of the killing induced by the soluble laminarin with the killing induced by the control, i.e. the unstimulated NK cells, shows significant differences at P 0.05 level (which means that each figure is provided with ±5%); thus, at ET 10:1, the soluble laminarin stimulated NK cells were 245% more cytotoxic, at ET 50:1 they were 196% more cytotoxic and at ET 100:1 they were 180% more cytotoxic than the control.

Similarly, when soluble laminarin stimulated NK cell killing was compared to Lentinan-stimulated NK cell killing, soluble laminarin was again found to be significantly more active at P 0.05 level: at ET 10:1 it was 133% at ET 50:1 it was 123% and at ET 100:1 it was 130% more active than lentinan.

The comparison with BEI-stimulated cell killing shows that soluble laminarin was again significally more active at P 0.05 level: at ET 10:1 it was 132%, at ET 50:1 it was 122%, and at ET 100:1 it was 129% more active than BEI.

Consequently, Laminarin clearly appears as being the most active of the three tested glucans.

These results thus clearly demonstrate that soluble laminarin has very strong stimulative effects on natural killer cells, which respond to the stimulation by enhanced killing of tumor cells.

The above said data have been confirmed by additional experiments where the effects of soluble laminarin on tumor growth in vivo were evaluated; yeast derived glucan BEI was used for comparison.

In these additional experiments, mice were inoculated with mouse breast cancer cell line 64 Ptas. Experimental treatment was achieved by daily intraperitoneal injection during 14 days of two different doses of soluble laminarin and BEI diluted in PBS; the said two different doses were respectively 100 and 250 μg of laminarin per injection.

At the end of the 14 days treatment, the mice were killed, tumors were removed and weighted.

In the case of the soluble laminarin treated mice, the weight of the tumors represented 28% with respect to the weight of the tumors treated with the control and in the case of BEI it represented 41% with respect to to the weight of the tumors treated with the control.

These results clearly demonstrate significant inhibition of cancer growth in laminarin treated mice as well as its superiority with respect to the effect obtained with BEI.

By way of consequence an object of the invention is consisting in a therapeutical method comprising administration to a patient of an effective amount of especially soluble laminarin for the treatment of tumors and more generally of cancers of the group comprising breast cancer, lung cancer, oesophagus cancer, stomach cancer, intestine and colon cancers, and for the treatment of viral, bacterial and fungal diseases as well as diseases related to immunostimulant deficiencies of human beings and warm-blood animals.

The expression "effective amount" designates throughout the specification the concentration or quantity or level of laminarin that can attain the contemplated medical end such as control or destruction of cancer cells or virally infected cells without producing unacceptable toxic symptoms; the said effective amount will vary with factors such as the particular condition being treated, the physical condition of the patient and the duration of the treatment.

Another object of the invention is consisting in a therapeutical method of treating, by stimulation of the NK cells of a patient, comprising administration to a patient of an effective amount of especially soluble laminarin of tumors and more generally of cancers of the group comprising breast cancer, lung cancer, oesophagus cancer, stomach cancer, intestine and colon cancers, and of viral bacterial and fungal diseases as well as diseases related to immunostimulant deficiencies of human being and warm-blood animals.

Applicants also have investigated the effect of laminarin on the production of TNF-alpha, i.e. tumor necrosis factor alpha which is a pleiotropic cytokine secreted primarily by monocyte/macrophages and T lymphocytes, respectively.

TNF-alpha was originally described as a factor present in the serum of Bacillus Calmette-Geurin-treated mice that induced tumor necrosis in tumor bearing mice.

TNF-alpha is the principal mediator of natural immunity against Gram-negative bacteria and a key mediator of inflammatory response and septic shock.

In addition, it has many other activities, including a cytotoxic effect toward certain target cells and tumors, induction of MHC "major histocompatibility complex" class I and II molecules on target cells, activation of polymorphonuclear leukocytes, and co-stimulatory effects on T and B lumphocytes.

Extracellular forms of TNF receptors are shed and appear in biological fluids, potentially acting as regulators of TNF activity; TNF activity means any biological activity, TNF can have on biological systems.

Older bioassays for TNF-alpha were based on its cytotoxic effects toward target cells. Recently, highly specific commercial kits made the evaluation of TNF-alpha production easier and more reliable.

By way of consequence it is thus of interest to stimulate the production of TNF-alpha and Applicants surprisingly and unexpectedly found that such a stimulation becomes possible when treating with laminarin especially soluble laminarin, an organism whose natural defenses against especially cancer through the action of TNF-alpha are to be improved.

Consequently, another object of the invention is consisting in a therapeutical method of treating, by stimulation of the production of TNF-alpha, comprising administration to a patient of an effective amount of especially soluble laminarin, of tumors and more generally of cancers of the group comprising breast cancer, lung cancer, oesophagus cancer, stomach cancer, intestine and colon cancers, and of viral, bacterial and fungal diseases as well as diseases related to immunostimulant deficiencies of human beings and warm-blood animals.

In connection with the experiments carried out in that respect by Applicants, Balb/c mice were intraperitoneally injected with 250 mg of laminarin or lentinan (purchased from Sigma St. Louis, Mo., USA) in PBS.

Mice of a control group were treated with PBS only.

After various time intervals (10, 30, 60 and 90 minutes, respectively), after the injection of laminarin, Lentinan and PBS only, the mice were killed and blood was collected in Eppendorf tubes.

Subsequently, the serum of the collected blood was separated, collected and stored at −80° C. for no more than 1 week.

The level of TNF-alpha in the serum samples was evaluated using a commercial kit marketed as OptEIA Mouse TNF-alpha (Mono/Mono) Set by the Company Pharmingen, San Diego, Calif. USA); the manufacturer's instructions were followed.

In that respect, wells of 96-well plates were coated with 0.1 ml/well of capture antibody (provided in the above kit) diluted in coating buffer (also provided in the above kit); the expression "capture antibody" designates first antibody used for coating of wells; this antibody captures the tested cytokines from the solution; in this assay it was anti-mouse-TNF-alpha monoclonal antibody.

The plates were sealed and incubated overnight at 4° C.

Individual wells were emptied by aspiration and washed 3 times with over 300 μl/well of wash buffer (also provided in the kit).

Reaction was blocked with 200 μl/well of assay diluent (also provided in the kit) and by incubation for 60 minutes at room temperature.

Again, individual wells were emptied by aspiration and washed 3 times with over 300 μl/well of the same wash buffer.

Standards (also provided in the kit) and samples of serum were diluted in assay diluent (also provided in the kit) and pipetted (100 μl/well) in appropriate wells; as far as the dissolution rate is concerned standards (part of the kit) were diluted according to the instructions into following concentrations: 1000 pg/ml, 500 pg/ml, 250, 125, 62.5, 31.3, and 15.6 pg/ml.

The plates were sealed with plastic foils and incubated for 60 minutes at room temperature. Individual wells were emptied by aspiration and washed 3 times with over 300 μl/well of same wash buffer.

A quantity of 100 μl/well of substrate solution (also provided in the kit) was added to each well and the plates were incubated for 30 minutes in the dark at room temperature; "substrate solution" is formed by mixing a substrate reagent A containing hydrogen peroxide and Substrate reagent B containing 3,3',5,5'-tetramethylbenzidine in organic solvent; when mixed together, the reagent reacts with peroxidase-labeled conjugates to develop a blue color.

A quantity of 50 μl/well of stop solution provided in the kit and adapted to stop the reaction was added to each well and the optical density was determined using a STL ELISA reader (marketed by Tecan U.S., Research Triangle Park, N.C.) at 450 nm with a correction at 570 nm.

The concentration of TNF-alpha, in pg/ml, in the blood of the mice treated as hereabove disclosed has been determined at the following moments: 10, 30, 60 and 90 minutes after the injection of soluble laminarin, Lentinan and control.

The values obtained are collected in Table II.

TABLE II

Concentration, in μg/ml of TNF-alpha in mice treated with 250 μg of Soluble laminarin, Lentinan or Control (values recorded and standard deviation)

| Duration (in minutes) between injection and measurement | 10 | 30 | 60 | 90 |
|---|---|---|---|---|
| soluble laminarin | 0 | 51.98 + 6.3 | 64.20 + 8.9 | 83.48 + 4.1 |
| Lentinan | 0 | 31.03 + 5.1 | 27.55 + 3.7 | 25.99 + 6.2 |
| Control | 0 | 1 | 0 | 2 |

FIG. 2 is a graph representing the variation of the concentration expressed in μg/ml of TNF-alpha in the blood of the experimental mice as a function of the duration t expressed in minutes of the action of either soluble laminarin, Lentinan or Control, these data being those of Table II.

In FIG. 2 the variations of TNF-alpha in the presence of soluble laminarin, Lentinan and Control are illustrated by respectively curves A, B and C.

The conclusions which can be drawn from the data collected in table II and from FIG. 2 are that the indirect activation of macrophages and cytotoxic T lymphocytes, measured as the increase of TNF-alpha secretion is significantly higher when using especially soluble laminarin instead of Lentinan.

From the two above described sets of experiments it appears that soluble laminarin has a double effect on immune reactions both specific via activation of NK cells and non specific via stimulation of TNF alpha production.

Consequently, Applicants have demonstrated that soluble laminarin therapy constitutes a promising treatment of various diseases including cancer and other diseases which comprise infection diseases such as bacterial, viral, fungal or opportunistic diseases, immune diseases, auto-immune diseases, allergic diseases, and all diseases in which the immune system in mammals needs to be stimulated.

The contemplated therapies involve the posologies and the pharmaceutical forms hereafter disclosed.

Dosages vary in a wide range depending essentially on the mode of administration.

In that respect when administrated intravenously the dosis of soluble laminarin is from about 0.1 to 10 mg per day.

In the case of the intraperitoneally mode the dosis is from 0.1 to about 50 mg/kg per day during a period of from 5 to 15 days; that period can possibly be reiterated.

By oral administration, the dosis varies from about 1 to about 100 and is preferably of about 10 mg/kg, advantageously twice a week over extended periods of time and possibly for the whole life of the patient.

In that respect, an object according to the invention is consisting in a therapeutical method of treating tumors and more generally cancers of the group comprising breast cancer, lung cancer, oesophagus cancer, stomach cancer, intestine and colon cancers, and viral, bacterial and fungal diseases as well as diseases related to immunostimulant deficiencies of human beings and warm-blood animals, by intravenous administration of an amount of from 0.1 to 10 mg per day of preferably soluble laminarin.

Another object according to the invention is consisting in a therapeutical method of treating tumors and more generally of cancers of the group comprising breast cancer, lung cancer, oesophagus cancer, stomach cancer, intestine and colon cancers, and of viral, bacterial and fungal diseases as well as diseases related to immunostimulant deficiencies of human beings and warm-blood animals, by intraperitoneally administration of from 0.1 to about 50 mg/kg per day during a period of from 5 to 15 days of preferably soluble laminarin.

Another object according to the invention is consisting in a therapeutical method of treating tumors and more generally of cancers of the group comprising breast cancer, lung cancer, oesophagus cancer, stomach cancer, intestine and colon cancers, and of viral, bacterial and fungal diseases as well as diseases related to immunostimulant deficiencies of human beings and warm-blood animals, by oral administration, of from 1 to 100 and, preferably, of about 10 mg/kg, advantageously twice a week over extended periods of time, of preferably soluble laminarin.

Laminarin, especially in its soluble form is considered as safe.

Its LD 50 is high and was determined as to be greater than 2000 mg/Kg given orally in rats; furthermore there are no special handling requirements.

The medicinal formulations according to the invention comprise an effective amount of soluble laminarin, and advantageously, a potentiator generally mixed with a pharmaceutically acceptable carrier.

By the term "potentiator" is designated a material that improves or increases the efficiency of laminarin or acts on the immune system as immuno-modulator and is used in combination with laminarin.

The "pharmaceutical acceptable carrier" is selected from the group comprising pharmaceutically acceptable solvents, suspending agents or vehicles, and in function of the route selected for administration, and keeping in mind standard pharmaceutical practice; "acceptable" means that the carrier is compatible with the other ingredients of the formulation and not injurious to the patient.

More generally, a "pharmaceutically acceptable component" should not present or induce undue adverse side effects such as toxicity, irritation, and allergic response and should be commensurate with a reasonable benefit/risk ratio.

Oral formulations suitable for use in connection with the present invention include capsules, gels, cachets, effervescent or non-effervescent powders, tablets, and granules; they may consist of a solution, of a suspension in an aqueous or non-aqueous liquid, of an oil-in-water liquid emulsion or of a water-in-oil emulsion.

The pharmaceutical forms through which laminarin is administered may also be presented as a bolus, an electuary, or a paste.

Generally, the said formulations may be prepared by uniformly mixing the active ingredient, i.e. especially soluble laminarin with liquid carriers or finely divided solid carriers or both, and then if necessary by shaping the product.

Suitable solid carriers comprise lactose, sucrose, gelatin, agar and bulk powders.

Suitable liquid carriers comprise water, pharmaceutically acceptable fats and oils, alcohol or other organic solvents, including esters, emulsions, syrups or elixirs, suspensions, solutions and/or suspensions, and solutions and or suspensions reconstituted from non-effervescent granules and effervescent preparations reconstituted from effervescent granules.

They also may comprise preservatives, emulsifying agents, suspending agents, diluents, sweeteners, thickeners, and melting agents; preferred liquid carriers are edible oils, for example, corn or canola oils, as well as polyethylene glycols or PEG.

The therapeutical forms, intended for oral administration, comprise non-toxic, pharmaceutically acceptable, inert carriers selected from the group comprising lactose, starch, sucrose, glucose, methyl cellulose, magnesium stearate, dicalcium phosphate, calcium sulfate, mannitol, sorbitol, cyclodextrin, and cyclodextrin derivatives.

Capsules or tablets containing laminarin according to the invention should preferably be easy to swallow or to chew, and contain carriers, binders, lubricants, diluents, disintegrating agents, coloring agents, flavoring agents, flow-inducing agents, or melting agents; they may be produced by compression or molding, optionally with one or more classical additional ingredients.

The tablets are optionally coated and may be formulated so as to provide slow- or controlled-release of the active ingredient. Tablets may also optionally be provided with an enteric coating to provide release in parts of the gut other than the stomach.

Laminarin may additionally be combined with chemotherapeutic agents, or potentiators, to provide a combination therapy.

Combination therapy can be sequential, that which means the treatment is carried out with one agent first and then with the second agent; or it can be a treatment with both agents at the same time. The sequential therapy can be performed within a reasonable time after the completion of the first therapy before beginning the second one. The treatment with both agents at the same time can be in the same daily dose or separate doses.

For example:

- in the case of retrovinal infection, a combination therapy may consist in treatment with soluble laminarin together with nucleosides analogues, (with inhibitors of reverse transcriptase), such as AZT or with proteases inhibitors such as Ritonavir.
- in the case of cancer diseases a combination therapy may consist in treatment with soluble laminarin together with topo-isomerase inhibitors, such as Topotecam, Antracyoline, or antimetabolites such a Cytarabine, Fluorouracil and others.

EXAMPLE A

Laminarin Containing Tablet

A large number of tablets are prepared by conventional procedures so that the dosage unit was 100 mg of active ingredient per tablet:

| | |
|---|---|
| soluble laminarin in lyophylised form | 100 mg |
| colloidal silicon dioxide | 0.2 mg |
| Magnesium stearate | 5 mg |
| Microcristalline cellulose | 270 mg |
| Starch | 10 mg |
| Mannitol | 98.8 mg |

Appropriate coating can be applied to increase palmabitlity and or delay absorption.

EXAMPLE B

Laminarin Containing Granules.

An amount of 1 liter of an aqueous solution containing 75 g of soluble laminarin is mixed with 10 g of dextrin, the thus obtained mixture being absorbed into a food base i.e. starch, sorbitol, carboxy-methyl-cellulose, lactose, mannitol, guar gum, vanilline.

The resulting powder is extruded to form an extrusion granulate using a net of 1 mm. The granules are sieved on a 12 mesh sieve and the resulting granules are dried at 60° C. overnight in a drier to provide granules containing about 25% by weight of laminarin and about 3% of moisture.

These granules are used as an additive to drinking water or the like. For example, for these granules, a posology of 6 to 9 tea spoons per day for and adult and 2 or 3 tea spoons per day for a children is recommended.

EXAMPLE C

Insoluble laminarin containing pharmaceutical forms for oral administration:

| | |
|---|---|
| 1-lozenges consisting of | |
| insoluble laminarin powder | 5 parties by weight |
| mannitol as flavored carrier | 20 parties by weight |
| starch | 25 parties by weight |
| sorbitol | 30 parties by weight |
| Sucrose | 20 parties by weight |
| 2-Mouthwashes | |
| laminarin | 1% |
| liquid carrier consisting of xylitol cristal, sodium cyclamatate, alcool, sorbic acid, mint aroma, menthol, eugenol, sodium parahydroxybenzoate and purified water. | |

EXAMPLE D

Soluble laminarin containing pharmaceutical form for vaginal administration; vaginal cream with 1% of soluble laminarin:

| | |
|---|---|
| Soluble laminarin | 1% |
| Excipient: vaseline, non-ionic emulsionable wax, liquid paraffine, glycine, sodium hydroxyde concentrated solution qsp pH = 4 to 5, sorbic acid, purified water. | |

EXAMPLE E

Soluble laminarin containing pharmaceutical form for rectal administration presented as a suppository with a formulation expressed per suppository:

| | |
|---|---|
| Soluble powder laminarin | 8 mg |
| Retinol concentrate or synthetic vitamine A in oily form | 1500 UI |
| Excipients: semi-synthetic glycerides | |

EXAMPLE F

Soluble laminarin containing pharmaceutical form for nasal administration which may be administrated in a liquid form, as a nasal spray.

| | |
|---|---|
| soluble laminarin | 1% |
| benzoic acid | 200 mg |
| Excipients: potassium sulfate, potassium hydroxyde, benzalkonium chloride, alcool, rosemary essential oil, purified water qsp. | |

EXAMPLE G

Soluble laminarin containing pharmaceutical form for parenteral administration as an injectable solution for an ampoule of 1 ml

| | |
|---|---|
| Soluble laminarin | 2 mg |
| Excipients: chlorhydric acid or sodium hydroxyde qsp pH: 5.0 to 7.5, USP water for injection | |

EXAMPLE H

Soluble laminarin containing veterinary formulation for example an udder gel with 5% of of soluble laminarin:

| | |
|---|---|
| Soluble laminarin | 5% |
| Salicylic acid | 1% |
| Excipients: propylene glycol, hypromellose, potassium sorbate, purified water | |

What is claimed is:

1. A therapeutical method comprising intravenous, intraperitoneal or oral administration of an amount of laminarin, comprised within a composition comprising laminarin and a pharmaceutically acceptable carrier, to a human or to a warm-blooded animal suffering from a tumor, a cancer, a viral disease, a bacterial disease, a fungal disease, a disease of the immune system, an auto-immune disease or a disease related to a deficiency of immunostimulation, in the human or the animal, wherein the amount of laminarin or the concentration of laminarin in the composition is effective to treat the tumor, the cancer or the disease.

2. The method of claim 1, wherein the laminarin is laminarin in soluble form.

3. The method of claim 1, wherein the cancer is claim breast cancer, lung cancer, esophageal cancer, stomach cancer, intestinal cancer or colon cancer.

4. The method of claim 1, wherein the administration of laminarin stimulates NK cells in the human or the animal.

5. The method of claim 1, wherein the administration of laminarin stimulates production of TNF-alpha in the human or the animal.

6. The method of claim 1, further comprising administration of a chemotherapeutic agent.

7. The method of claim 1, further comprising administration of a potentiator.

8. The method of claim 1, wherein the administration comprises intravenous administration of an amount of laminarin of from about 0.1 mg/kg per day to about 10 mg/kg per day.

9. The method of claim wherein the administration comprises intraperitoneal administration of an amount of laminarin of from about 0.1 mg/kg per day to about 50 mg/kg per day during a period from 5 to 15 days.

10. The method of claim 1, wherein the administration comprises oral administration of an amount of laminarin of from about 1 mg/kg twice per week to 100 mg/kg twice per week.

11. The method of claim 1, wherein the administration comprises oral administration of an amount of laminarin of about 10 mg/kg twice a week.

* * * * *